(12) United States Patent
Gaset Vinaixa et al.

(10) Patent No.: US 7,410,624 B2
(45) Date of Patent: Aug. 12, 2008

(54) DEVICE FOR INTRODUCING ACTIVE SUBSTANCES INTO AMBIENT AIR

(75) Inventors: Pedro Gaset Vinaixa, Martorell (ES); Jorge Miró Amenós, Barcelona (ES)

(73) Assignee: Sara Lee/DE N.V. (NL)

( * ) Notice: Subject to any disclaimer, the term of this patent is extended or adjusted under 35 U.S.C. 154(b) by 688 days.

(21) Appl. No.: 10/332,449

(22) PCT Filed: Jul. 10, 2001

(86) PCT No.: PCT/NL01/00526

§ 371 (c)(1),
(2), (4) Date: Jul. 14, 2003

(87) PCT Pub. No.: WO02/04035

PCT Pub. Date: Jan. 17, 2002

(65) Prior Publication Data

US 2004/0029059 A1     Feb. 12, 2004

(30) Foreign Application Priority Data

Jul. 10, 2000    (NL) .................................. 1015675

(51) Int. Cl.
*A61L 9/00* (2006.01)
*A62B 7/08* (2006.01)
*F24F 6/08* (2006.01)

(52) U.S. Cl. .................. 422/306; 422/1; 422/5; 422/28; 422/123; 422/125; 422/126; 422/305; 422/900; 395/395; 395/386

(58) Field of Classification Search ................ 422/1, 422/5, 28, 123, 125–126, 305–306, 900; 392/395, 386
See application file for complete search history.

(56) References Cited

U.S. PATENT DOCUMENTS

| | | | | | |
|---|---|---|---|---|---|
| 2,184,803 | A | * | 12/1939 | Harris et al. | 221/148 |
| 2,510,449 | A | * | 6/1950 | Williams et al. | 422/125 |
| 2,521,942 | A | * | 9/1950 | Pearsall | 422/305 |
| 2,677,948 | A | * | 5/1954 | Gehrie | 431/143 |
| 4,178,346 | A | * | 12/1979 | Allen et al. | 422/126 |
| 4,198,375 | A | * | 4/1980 | Rogers | 422/126 |
| 4,324,763 | A | * | 4/1982 | Jarman | 422/116 |

FOREIGN PATENT DOCUMENTS

| | | | |
|---|---|---|---|
| EP | 0 268 114 | | 5/1988 |
| GB | 2 073 020 A | * | 4/1980 |
| GB | 1239498 | | 11/1984 |
| WO | WO 86/01980 | | 4/1986 |

\* cited by examiner

*Primary Examiner*—Jill Warden
*Assistant Examiner*—Monzer R Chorbaji
(74) *Attorney, Agent, or Firm*—Altera Law Group, LLC

(57) ABSTRACT

A device for introducing active substances, such as aromatic substances, insecticides and the like, into ambient air, comprises a holder for a carrier with a wick impressed thereon, which carrier can be placed in the holder and is replaceable. A mechanism to be operated by hand is provided for operating an ignition element, which can be placed in the holder and is replaceable, as for instance a gas lighter, to enable a wick to be ignited when a carrier with this wick has been placed in the holder.

12 Claims, 2 Drawing Sheets

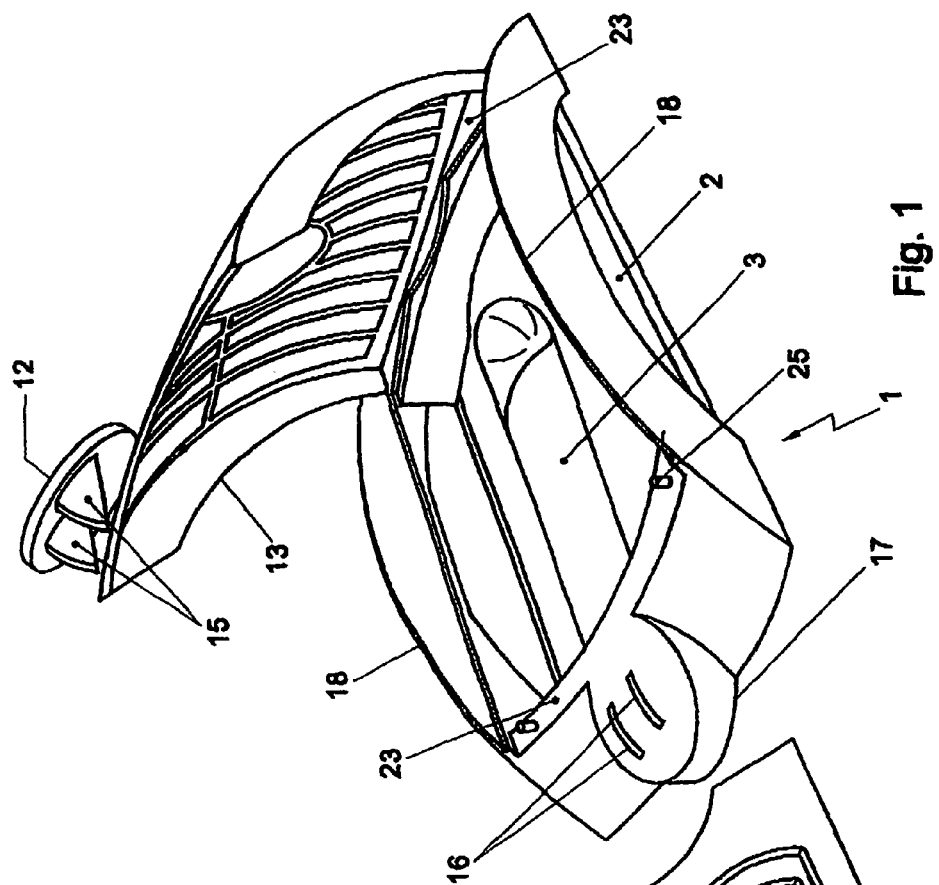
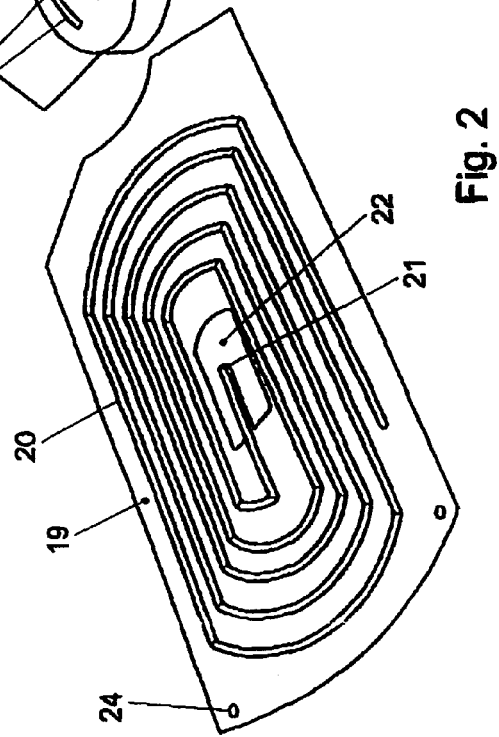
Fig. 1
Fig. 2 under construction>
DEVICE FOR INTRODUCING ACTIVE SUBSTANCES INTO AMBIENT AIR

The present invention relates to a device for introducing active substances such as aromatic substances, insecticides and the like, into ambient air, comprising a holder for a carrier with a wick impressed thereon.

Carriers with a wick impressed thereon are known; the wick may be made on a carbon base, with charcoal and wood pulp used as basic ingredients, while the desired active substances have been added for spreading aromatic substances, insecticides and the like, as well as further substances for realizing, a desired rate of combustion. The wick must be lighted by hand.

To facilitate the use of such a device and likewise increase safety, the device is characterized in that a mechanism to be operated by hand is provided for operating, an ignition element, which can be placed in the holder and is replaceable, to enable a wick to be ignited when a carrier with this wick has been place in the holder.

An embodiment advantageous in terms of price and easy to operate is obtained when the holder is suitable for placing a gas lighter therein, which gas lighter can be operated by means of the above mechanism. The simplest and cheapest gas lighter may be chosen.

A practical embodiment of the above mechanism is obtained when this is formed by a control button, by means of which the housing of a gas lighter placed in the holder can be moved relative to an ignition push button provided on this gas lighter. Normally, such a gas lighter can be operated by pressing the ignition push button relative to the housing tightly held in the hand.

To prevent a carrier from being wrongly placed in the holder, the device is provided with fitting means to enable the carrier to be placed in the holder in a fixedly defined position. Besides, clamping means may be provided to enable a carrier placed in the holder to be clamped in its fixedly defined position.

To efficiently deliver the active substances to the ambient air, the holder may be provided with openings arranged in the upper surface of the holder above the place intended for the carrier.

The invention not only relates to a device for introducing active substances into ambient air but also to a carrier suitable for being placed in the holder of such a device, which carrier is provided with an impressed wick in which active substances are included which, when this wick is burning, are released and delivered to the ambient air. According to the invention, the shape of this carrier is adapted to the supporting surface therefor on the inner side of the holder.

Around the right place where the ignition of the wick has to occur, a recess is provided in the carrier near one end of the wick impressed thereon, which recess is of such a size and in such a position that, when activating the ignition element, only this wick end is ignited.

The carrier may further be provided with fitting means which, when placing the carrier in the holder, can cooperate with the fitting means of the holder.

Finally, the invention relates to a combination of a device and a carrier as described above and an ignition element, preferably a gas lighter, as mentioned above.

The invention will now be explained in more detail on the basis of the exemplary embodiment shown in the accompanying drawing. In this drawing:

FIG. 1 shows a device according to the invention for introducing active substances into ambient air;

FIG. 2 shows a carrier with an impressed wick to be arranged therein; and

Figure 3:
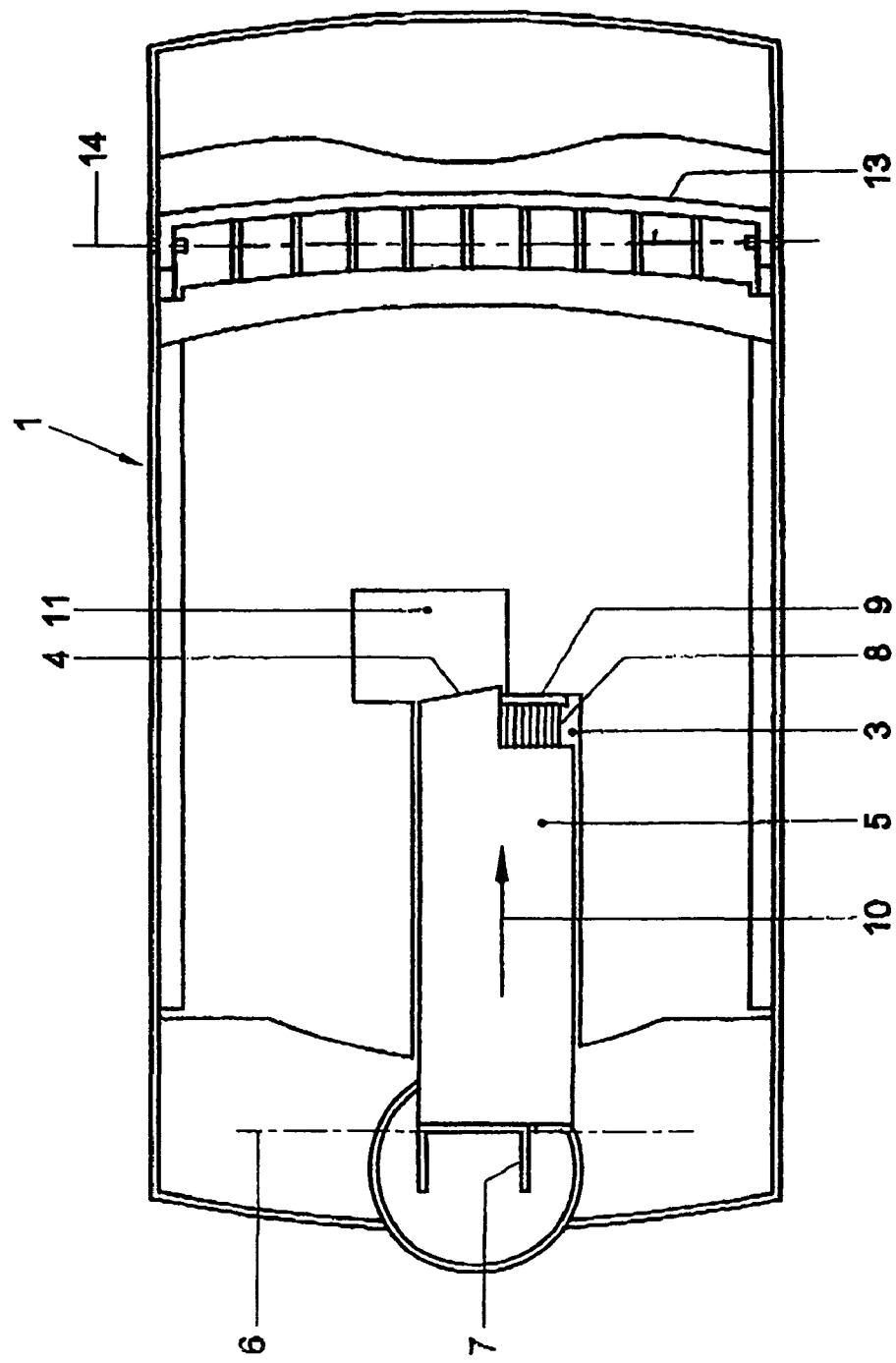
FIG. 3 shows the device according to the invention from below.

In the exemplary embodiment shown in FIGS. 1 and 3, the device according to the invention is formed by a holder 1 with a bottom plate 2, in which an upwardly directed, elongated hollow space 3 is provided. From below a gas lighter 4 can be placed in this hollow space 3. Housing 5 of this gas lighter rests against a support 7, which can hinge around line 6, while the ignition push button 8 of lighter 4 rests against a supporting edge 9 of bottom plate 2. By tilting support 7 around line 6 against spring force, housing 5 can be moved in the direction of arrow 10. This means that ignition push button 8 is pressed relative to this housing 5 and lighter 4 ignites. In space 11 in bottom plate 2 an upwardly deflected flame is thus obtained, which is extinguished when support 7, by spring action, returns to the position shown in FIG. 3 and the housing 5, by the built-in spring action in the gas lighter, moves backwards against the direction of arrow 10 relative to ignition push button 8. Support 7 can be tilted against spring pressure by means of a push button 12. This control push button 12 is fixed to a cover 13, which is arranged in holder 1 and can hinge around line 14. Push button 12 is provided with two triangular linkage lips 15, which, when cover 13 is moved down, fit into two corresponding slits 16 in an operating member 17 of holder 1. Push button 12 can be moved down relative to cover 13 against spring action. When holder 1 is closed, push button 12 can therefore be pushed further down against spring action, with the edges of the triangular lips 15 abutting against the edges of support 7 and causing this support to tilt against spring action.

In the present exemplary embodiment, the holder is provided with arch-shaped side edges 18, while cover 13 is curved accordingly and is provided with a lattice structure.

A carrier 19 provided with an impressed wick 20 can be placed in holder 1. FIG. 2 shows such a carrier, in which the wick is spirally arranged. Other forms for the wick are of course possible, for instance a meandering wick. The wick is made on a carbon base and provided with active substances, as for instance aromatic substances or insecticides, which, when the wick is burning, are released and delivered to the ambient air. It will be clear that the length of the wick determines the life of the carrier. The lattice structure in cover 13 serves to facilitate the delivery of the active substances from the top of holder 1 to the ambient air. Around the end 21 of the carrier 19 a recess 22 is arranged in the carrier. The place of this end 21 is such that, when carrier 19 is arranged in holder 1, this end ignition point comes to lie approximately above the place where the flame of gas lighter 4 is obtained. Holder 1 has flat edges 23, on which carrier 19 can be placed. As shown in FIGS. 1 and 2, the shape of the circumference of carrier 19 is adapted to these edges 23. Edges 23, together with corresponding lower edges in cover 13, can form clamping means, between which the carrier can be clamped. Carrier 19 and holder 1 are further provided with respectively fitting means 24 in the form of holes and 25 in the form of protuberances, so that the carrier is always laid in the holder in a fixedly defined position.

It is further noted that, although not shown in the figures, a cover may be provided for closing the hollow space 3, into which the gas lighter fits, and the bottom side of the operating member 17.

Both carrier 19 and gas lighter 4 are replaceable constituent parts in the whole.

The invention is not limited to the exemplary embodiment described herein with reference to the drawings, but comprises all kinds of modifications thereof, of course as far as falling within the scope of protection of the appended claims.

The invention claimed is:

1. A device for introducing active substances, chosen from the group consisting of aromatic substances and insecticides into ambient air, comprising:
 a carrier with a wick impressed thereon;
 a holder having an exterior for the carrier with the wick impressed thereon;
 a replaceable ignition element placed in the holder to enable the wick to be ignited;
 a mechanism operable by hand for operating the ignition element to enable the wick to be ignited;
wherein the ignition element is a gas lighter having a housing and an ignition push button and the mechanism comprises a control button accessible from the exterior by means of which the housing of the gas lighter and the push button are moved relative to each other; and
wherein the wick further includes an impressed wick in which active substances are included which, when said wick is burning, are released and delivered to ambient air, wherein the shape of the carrier is adapted to the supporting surfaces therefore on the inner side of the holder.

2. A device according to claim 1, wherein it is provided with fitting means keep the carrier placed in the holder in a fixed defined position.

3. A device according to claim 2, wherein it is provided with clamping means to clamp the carrier placed in the holder in a fixedly defined position.

4. A device carrier according to claim 1, wherein the carrier near one end of the wick impressed thereon a recess is provided, which is of such a size and in such a position that, when activating the ignition element, only this wick end is ignited.

5. A device carrier according to claim 1, wherein it is provided with fitting means, which, when placing the carrier in the holder, can cooperate with the fitting means of the holder.

6. A combination of a device according to claim 1, a carrier suitable for being placed in the holder, provided with an impressed wick in which active substances are included which, when said wick is burning, are released and delivered to the ambient air, wherein the shape of the carrier is adapted to the supporting surface therefore on the inner side of the holder, and an ignition element which can be placed in the holder and is replaceable, to enable a wick to be ignited when a carrier with this wick has been placed in the holder.

7. A device for introducing substances into ambient air, comprising:
 a removable and replaceable carrier having a wick applied thereon, said wick having a starting point thereon;
 a holder for receiving said wick; said holder having an interior and exterior; wherein said carrier is receivable substantially within said interior;
 a replaceable ignition element placeable in the holder, said ignition element having an igniting point, and wherein said igniting point is adjacent said wick starting point when said ignition element is placed in said holder;
 said holder further including a control button accessible from said exterior of said holder, linkage connected to said control button capable of actuating said ignition element in response to actuation of said button,
wherein said wick includes an impressed wick in which active substances are included which, when said wick is burning, are released and delivered to ambient air, wherein the shape of the carrier is adapted to the supporting surfaces therefore on the inner side of the holder;
 so that when said control button is actuated, said wick is ignited.

8. The device of claim 7 wherein said linkage includes at least one driving lip which extends from said control button, passes from the exterior of said holder and is engageable with said ignition element.

9. The device of claim 8, wherein said linkage includes a pair of wedge shaped elements and wherein said housing includes a pair of spaced apart apertures, sized to receive said wedge shaped elements, so that said elements many pass into said holder on actuation.

10. The device of claim 7 wherein said linkage moves said ignition element into engagement with said housing thereby igniting same at said ignition point.

11. The device of claim 7, where said linkage is configured to apply pressure against said ignition element when said control button is actuated and wherein said ignition element is triggered at said ignition point by impingement with said holder in response to said pressure.

12. The device of claim 11 wherein said ignition element is a gas lighter having an ignition trigger on one end and wherein said impingement causes said trigger to be activated.

* * * * *